United States Patent
Arruda et al.

(10) Patent No.: US 7,687,541 B2
(45) Date of Patent: Mar. 30, 2010

(54) PRODRUGS OF DIARYL-2-(5H)-FURANONE CYCLOOXYGENASE-2 INHIBITORS

(75) Inventors: Jeannie M. Arruda, San Diego, CA (US); Benito Munoz, San Diego, CA (US); Brian A. Stearns, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 949 days.

(21) Appl. No.: 10/574,655

(22) PCT Filed: Oct. 18, 2004

(86) PCT No.: PCT/US2004/034374

§ 371 (c)(1),
(2), (4) Date: Mar. 31, 2006

(87) PCT Pub. No.: WO2005/042476

PCT Pub. Date: May 12, 2005

(65) Prior Publication Data

US 2007/0123587 A1 May 31, 2007

Related U.S. Application Data

(60) Provisional application No. 60/513,284, filed on Oct. 22, 2003.

(51) Int. Cl.
| | |
|---|---|
| A61K 31/215 | (2006.01) |
| A61K 31/235 | (2006.01) |
| A61K 31/19 | (2006.01) |
| A61K 31/195 | (2006.01) |
| C07C 315/00 | (2006.01) |

(52) U.S. Cl. .................. 514/529; 514/533; 514/557; 514/562; 560/11; 562/427; 562/429

(58) Field of Classification Search .............. 562/427, 562/429; 560/11; 514/529, 533, 557, 562
See application file for complete search history.

(56) References Cited

U.S. PATENT DOCUMENTS 5,807,873 A    9/1998  Nicolai et al.

*Primary Examiner*—Taylor Victor Oh
(74) *Attorney, Agent, or Firm*—Curtis C. Panzer; Valerie J. Camara

(57) ABSTRACT

The invention encompasses the novel compounds of Formula (I) and Formula (II), which are prodrugs that convert in vivo to diaryl-2-(5H)-furanones useful in the treatment of cyclooxygenase-2 mediated diseases. These prodrugs are far more soluble in aqueous media than the active agents into which they convert, in vivo. As such compounds of Formula (I) and (II) are advantageous for, among other things intravenous administration. The invention also encompasses certain pharmaceutical compositions and methods for treatment of cyclooxygenase-2 mediated diseases comprising the use of compounds of Formula (I) and Formula (II).

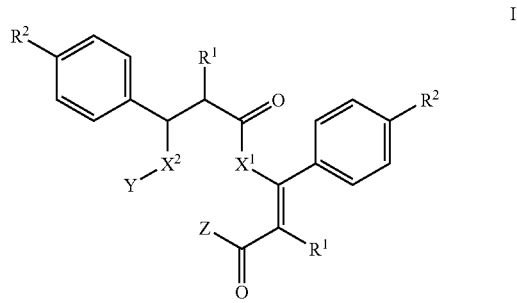

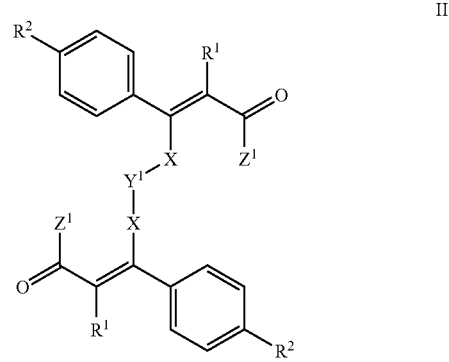

18 Claims, No Drawings

PRODRUGS OF DIARYL-2-(5H)-FURANONE CYCLOOXYGENASE-2 INHIBITORS

CROSS REFERENCE TO RELATED APPLICATIONS

This application is a U.S. National Phase application under 35 U.S.C. §371 of PCT Application No. PCT/US2004/034374 filed 18 Oct. 2004, which claims priority Under 35 U.S.C. 119 to U.S. Provisional Application Nos. 60/513,284 filed 22 Oct. 2003.

BACKGROUND OF THE INVENTION

The invention relates to the field of non-steroidal anti-inflammatory agents, and in particular, to prodrugs of diaryl-2-(5H)-furanones.

Selective inhibitors of cyclooxygenase-2 are a sub-class of the class of drugs known as non-steroidal antiinflammatory drugs (NSAIDs). The NSAIDs are active in reducing the prostaglandin-induced pain and swelling associated with the inflammation process but are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandin by inhibiting enzymes in the human arachidonic acid/prostaglandin pathway including the enzyme cyclooxygenase (COX). The discovery that there are two isoforms of the COX enzyme, the first, COX-1, being involved with physiological functions and the second, COX-2, being induced in inflamed tissue, has given rise to a new approach. While conventional NSAIDs block both forms of the enzyme, the identification of the inducible COX-2 enzyme associated with inflammation has provided a viable target of inhibition which more effectively reduces inflammation and produces fewer and less drastic side effects. Many compounds which have activity as COX-2 inhibitors have been identified, including rofecoxib (VIOXX®), etoricoxib (ARCOXIA™), celecoxib (CELEBREX®) and valdecoxib (BEXTRA™), and much research continues in this area.

SUMMARY OF THE INVENTION

The invention encompasses novel compounds of Formula I and Formula II, which are prodrugs of diaryl-2-(5H) furanones, and are therefore useful in the treatment of cyclooxygenase-2 mediated diseases.

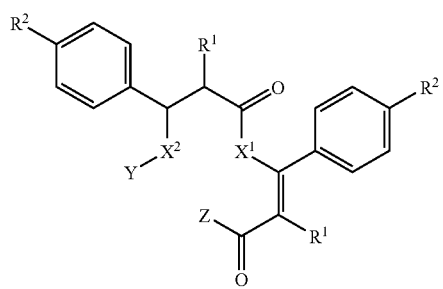

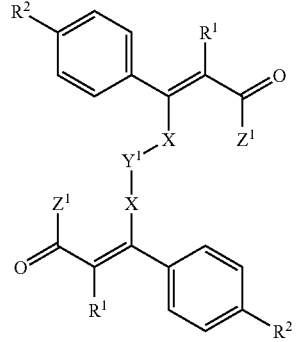

The invention also encompasses certain pharmaceutical compositions and methods for treatment of cyclooxygenase-2 mediated diseases comprising the use of compounds of Formula I and Formula II.

DETAILED DESCRIPTION OF THE INVENTION

The invention encompasses the novel compounds of Formula I and Formula II, which are prodrugs that convert in vivo to diaryl-2-(5H)-furanones useful in the treatment of cyclooxygenase-2 mediated diseases. These prodrugs are far more soluble in aqueous media than the active agents into which they convert, in vivo. As such compounds of Formula I and II are advantageous for, among other things intravenous administration.

In one embodiment, the invention is directed to compounds of Formula I

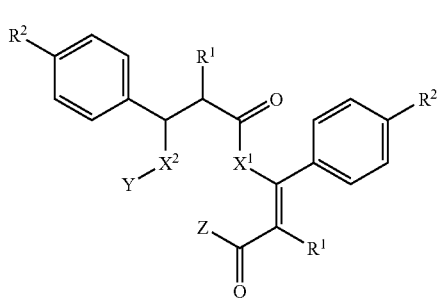

and pharmaceutically acceptable salt thereof, wherein
$R^1$ is
  (a) phenyl, optionally substituted at positions 3 and 4 halogens,
  (b) —O-isopropyl,
  (c) —O-cyclopropyl, and
  (d) —O—$CH_2$-cyclopropyl;
$R^2$ is selected from the group consisting of:
  (a) —$S(O)_2CH_3$, and
  (b) —$S(O)_2NH_2$;
$R^3$ is selected from the group consisting of
  (a) hydrogen,
  (b) methyl,
  (c) ethyl,
  (d) hydroxyl,
  (e) F, Cl, and
  (f) $CF_3$;

R[4] is selected from the group consisting of
(a) methyl, and
(b) ethyl;
X[1] is selected from the group consisting of:
(a) —OCH$_2$—,
(b) —OC(R[3])(R[4])—,
(c) —CH$_2$-linker —O—, and
(d) —C(R[3])(R[4])-linker-O—, wherein the oxygen end of X[1] is attached to the carbonyl carbon of Formula I;
X[2] is selected from the group consisting of:
(a) —OCH$_2$—,
(b) —OC(R[3])(R[4])—,
(c) —CH$_2$-linker —O—, and
(d) —C(R[3])(R[4])-linker-O—, wherein the carbon end of X[2] is attached to the carbon adjacent to the R[2]-phenyl of Formula I;
-linker— includes, but is not limited to a member of the group consisting of
(a) —C(O)—(CH2)$_m$—O—,
(b) —C(O)—(CH2)$_m$(—O—(CH$_2$)n)p-O—,
(c) —C(O)-aryl-O—,
(d) —C(O)-heteroaryl-O—, wherein m, n and p are each independently integers ranging from 0 to 6;
Y is selected from the group consisting of
(a) hydrogen, and
(b) acyl, wherein the acyl group includes, but is not limited to a member of the group consisting of
(a) —C(O)—C$_{1-6}$alkyl, optionally substituted with 1, 2 or 3 substituents independently selected from the group consisting of halo, hydroxyl, amino, C$_{1-3}$alkoxy, aminoC$_{1-3}$alkyl,
(b) —C(O)-aryl,
(c) —C(O)-heteroaryl,
(d) an amino acid;
Z is selected from the group consisting of:
(a) —OR[5], and
(b) —NR[5]R[6], wherein R[5] and R[6] are each independently selected from
(a) hydrogen,
(b) C$_{1-6}$alkyl,
(c) phenyl, and
(d) C$_{1-2}$-phenyl, wherein R[5] and R[6] choices (b), (c) and (d) are optionally substituted with 1, 2, or 3 substituents selected from halo, hydroxyl, amino, C$_{1-3}$alkyl, and C$_{1-3}$alkoxy.

Within this embodiment there is a genus wherein R[1] is phenyl, optionally substituted at positions 3 and 4 with fluorine.

Within this embodiment there is another genus wherein R[2] is —S(O)$_2$CH$_3$.

Within this embodiment there is another genus wherein R[3] is selected from the group consisting of
(a) hydrogen,
(b) methyl, and
(c) ethyl.

Within this embodiment there is a genus wherein X[1] and X[2] are each selected from the group consisting of:
(a) —OCH$_2$—, and
(b) —OC(R[3])(R[4])—.

Within this embodiment there is a genus wherein Y is hydrogen or —OCH$_3$.

Within this embodiment there is a genus wherein Z is hydroxyl or —OCH$_3$.

In another embodiment, the invention encompasses compounds of Formula II

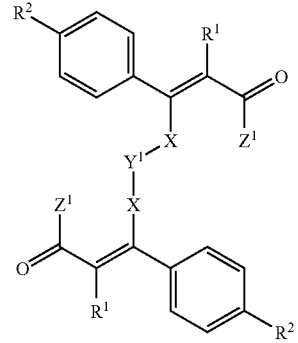

II

R[1] is
(a) phenyl, optionally substituted at positions 3 and 4 halogens,
(b) —O-isopropyl,
(c) —O-cyclopropyl, and
(d) —O—CH$_2$-cyclopropyl;
R[2] is selected from the group consisting of:
(a) —S(O)$_2$CH$_3$, and
(b) —S(O)$_2$NH$_2$;
X is selected from the group consisting of:
(a) —OCH$_2$—, and
(b) —C(R[3])(R[4])O—, wherein the carbon end of X is attached to the carbon adjacent to the R[2]-phenyl;
Y[1] is -linker1-, which includes, but is not limited to
(a) —C(O)—(CH$_2$)$_r$—C(O)—,
(b) —C(O)-aryl-C(O)—,
(c) —C(O)-heteroaryl-C(O)—,
(d) —C(O)—(CH$_2$)$_r$—(O—(CH$_2$)$_s$)$_t$—C(O)—,
(e) —C(O)—(CH$_2$)$_r$—CH—(CH$_2$)$_s$—C(O)—, wherein r, s and t are each independently integers ranging from 0 to 6.
Z[1] is selected from the group consisting of:
(a) —OR[5], and
(b) —NR[5]R[6], wherein R[5] and R[6] are each independently selected from
(a) hydrogen,
(b) C$_{1-6}$alkyl,
(c) phenyl, and
(d) C$_{1-2}$-phenyl, wherein R[5] and R[6] choices (b), (c) and (d) are optionally substituted with 1, 2, or 3 substituents selected from halo, hydroxyl, amino, C$_{1-3}$alkyl, and C$_{1-3}$alkoxy.

Within this embodiment there is a genus wherein R[1] is phenyl, optionally substituted at positions 3 and 4 with fluorine.

Within this embodiment there is another genus wherein R[2] is —S(O)$_2$CH$_3$.

Within this embodiment there is another embodiment wherein
$R^3$ is selected from the group consisting of
(a) hydrogen,
(b) methyl, and
(c) ethyl.

Within this embodiment there is a genus wherein
$Y^1$ is selected from the group consisting of
(a) —C(O)—(CH$_2$)$_r$—(O)—, and
(b) —C(O)—(CH$_2$)$_r$—CH—(CH$_2$)$_s$—C(O)—.

Within this embodiment there is a genus wherein
$Z^1$ is hydroxyl or —OCH$_3$.

Illustrating the invention is Example 1 and the compounds of Table 1 and Table 2.

The invention also encompasses a method of treating an inflammatory disease susceptible to treatment with a non-steroidal anti-inflammatory agent comprising administering to a patient in need of such treatment of a non-toxic therapeutically effective amount of a compound of Formula I or Formula II. Another embodiment of the invention encompasses method of treating cyclooxygenase mediated diseases advantageously treated by an active agent that selectively inhibits COX-2 in preference to COX-1 comprising administering to a patient in need of such treatment of a non-toxic therapeutically effective amount of a compound of Formula I or Formula AI.

Within this embodiment is encompassed the above method wherein the cyclooxygenase-2 selective mediated disease or condition is selected from the group consisting of: osteoarthritis, rheumatoid arthritis, acute, non-chronic and chronic pain, fever, dysmenorrheal, stroke ans spesis.

The invention also encompasses a pharmaceutical composition comprising a compound of Formula I or Formula II in combination with a pharmaceutically acceptable carrier.

As indicated above, compounds of Formula I and Formula II are prodrugs of diaryl-2-(5H)-furanones, which are selective inhibitors of cyclooxygenase 2 (COX-2) In vivo, the linking groups moieties (i.e. "-linker-" and "-linker1-"), will cleave from the parent molecule and the remaining portions will cyclize to yield two molecules of the desired diaryl-2-(5H)-furanones for every molecule of compound of Formula I or Formula II. In the amounts liberated, the linking group moieties lack significant in vivo biological activity The term "aryl" unless specifically stated otherwise includes multiple ring systems as well as single ring systems such as, for example, phenyl or naphthyl.

The term "hereroaryl" include, for example, pyridinyl, quinolinyl, isoquinolinyl, pyridazinyl, pyrimidinyl, pyrazinyl, quinoxalinyl, furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

For purposes of this specification alkyl is defined to include linear, branched, and cyclic structures, with $C_{1-6}$alkyl including including methyl, ethyl, propyl, 2-propyl, s- and t-butyl, butyl, pentyl, hexyl, 1,1-dimethylethyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$alkylthio is intended to include alkylthio groups of from 1 to 6 carbon atoms of a straight, branched or cyclic configuration. Examples of lower alkylthio groups include methylthio, propylthio, isopropylthio, cycloheptylthio, etc. By way of illustration, the propylthio group signifies —SCH$_2$CH$_2$CH$_3$.

For purposes of this specification, "acyl" is defined as the radical provided by residue of an organic acid after the removal of the hydroxyl from the organic acid.

Some of the compounds described herein contain olefinic double bonds, and unless specified otherwise, are meant to include both E and Z geometric isomers.

The term "treating a chronic cylcooxygenase-2 mediated disease or condition" means treating or preventing any chronic disease or condition that is advantageously treated or prevented by inhibiting the cyclooxygenase-2 enzyme. The term includes the relief of pain, fever and inflammation of a variety of conditions including rheumatic fever, symptoms associated with influenza or other viral infections, common cold, low back pain, neck pain, dysmenorrhea, headache, migraine, toothache, sprains and strains, myositis, neuralgia, synovitis, arthritis, including rheumatoid arthritis, degenerative joint diseases (osteoarthritis), gout, ankylosing spondylitis, bursitis, burns, injuries, and pain and inflammation following surgical procedures. In addition, such a compound may inhibit cellular neoplastic transformations and metastatic tumor growth and hence can be used in the treatment and/or prevention of cancer. In addition, such a compound may inhibit the onset or progression of Altzheimer's disease or cognitive impairment. The term also includes the treatment and/or prevention of cyclooxygenase-mediated proliferative disorders such as may occur in diabetic retinopathy and tumor angiogenesis. The term "treating" encompasses not only treating a patient to relieve the patient of the signs and symptoms of the disease or condition but also prophylactically treating an asymptomatic patient to prevent the onset or progression of the disease or condition.

The term "amounts that are effective to treat" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician. The inhibitor of cyclooxygenase-2 may be administered at a dosage level up to conventional dosage levels for NSAIDs. Suitable dosage levels will depend upon the antiinflammatory effect of the chosen inhibitor of cyclooxygenase-2, but typically suitable levels will be about 0.001 to 50 mg/kg per day, preferably 0.005 to 30 mg/kg per day, and especially 0.05 to 10 mg/kg per day. The compound may be administered on a regimen of once or twice per day.

The term "amount effective to reduce the risk of" means the amount of a pharmaceutical drug that will prevent or reduce the risk of occurrence of the biological or medical event that is sought to be prevented in a tissue, a systems animal or human by a researcher, veterinarian, medical doctor or other clinician. Aspirin is administered at a dose of about 30 mg to about 1 g once daily, preferably at a dose of about 80 mg to about 650 mg.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The Compound of Formula I and Formula II are useful for the relief of pain, fever and inflammation of a variety of conditions including rheumatic fever, symptoms associated with influenza or other viral infections, common cold, low back and neck pain, dysmenorrhea, headache, migraine, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compounds of Formula I and Formula II may also be useful for the treatment of dementia including pre-senile and senile dementia, and in particular, dementia associated with Alzheimer Disease (i.e. Alzheimer's dementia). Compounds of Formula I and Formula II may also be useful in the treatment of stroke and sepsis.

Compounds of Formula I and Formula II will also inhibit prostanoid-induced smooth muscle contraction by preventing the synthesis of contractile prostanoids and hence may be of use in the treatment of dysmenorrhea, premature labor and asthma. They will also be useful to inhibit bone loss (osteoporosis).

By virtue of its high cyclooxygenase-2 (COX-2) activity and/or its selectivity for cyclooxygenase-2 over cyclooxygenase-1 (COX-1) as defined above, compounds of Formula I and Formula II will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (e.g. impaired renal function); those prior to surgery or taking anticoagulants; and those susceptible to NSAID induced asthma.

Similarly, compounds of Formula I and Formula II, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I and Formula II as defined above and one or more ingredients such as another pain reliever including acetaminophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I and Formula II, optionally co-administered with one or more of such ingredients as listed immediately above.

Compounds of the present invention are inhibitors of cyclooxygenase-2 and are thereby useful in the treatment of cyclooxygenase-2 mediated diseases as enumerated above. This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a compound of Formula I or Formula II. The $IC_{50}$ values represent the concentration of inhibitor required to return $PGE_2$ synthesis to 50% of that obtained as compared to the uninhibited control. For the treatment of any of these cyclooxygenase mediated diseases, compounds of Formula I or Formula II may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I and Formula II may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I or Formula II are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Assays for Determining Biological Activity

The compounds of Formula I may be tested using the following assays to determine their biological activity.

Inhibition of Cyclooxygenase Activity

Compounds are tested as inhibitors of cyclooxygenase activity in whole cell and microsomal cyclooxygenase assays. Both of these assays measure prostaglandin $E_2$ ($PGE_2$) synthesis in response to arachidonic acid, using a radioimmunoassay. Cells used for whole cell assays, and from which microsomes are prepared for microsomal assays, are human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate addition. $IC_{50}$ values represent the concentration of putative inhibitor required to return $PGE_2$ synthesis to 50% of that obtained as compared to the uninhibited control.

1. Microsomal Cyclooxygenase Assay

Cox microsomal fractions are prepared as previously described (Percival et al., Arch. Biochem. Biophys. (1994) 315:111-118). The enzyme reactions are performed in 50 mM KPi pH 8.0, 1 µM heme, 1 mM phenol supplemented with 10 µg/ml of each Cox-1 or Cox-2 microsomal fractions. 1 µl DMSO or test compound (100 fold stock concentrated in DMSO) are added to 100 µl buffer. The enzyme reaction is initiated 15 minutes later by the addition of 10 µl of 100 µM arachidonic acid. The enzyme reaction is allowed to proceed for 5 minutes at room temperature before being stopped by the addition of 10 µl 1 N HCl. $PGE_2$ levels are then determined by EIA (Assay Designs) using the manufacturer's instruction.

By way of example, the Compounds of Formula I and Formula II, will general demonstrate $IC_{50}$ values of >100 µM against both microsomal human COX-1 and COX-2. This demonstrates that the unconverted pro drug is inactive against both COX-1 and COX-2.

Human Whole Blood Cyclooxygenase Assay

Assays are performed as described in Brideau et al. (1996) Inflammation Res.

1. COX-2 (LPS-induced $PGE_2$ Production):

Fresh blood is collected in heparinized tubes by venipuncture from healthy male volunteers. These subjects had no apparent inflammatory conditions and had not taken any NSAIDs for at least 7 days prior to blood collection. The blood is initially pre-incubated with bacterial lipopolysaccharide (LPS) at 100 µg/ml (Sigma Chem, #L-2630 from *E. coli*, serotype 0111:B4; diluted in 0.1% w/v bovine serine albumin in phosphate buffered saline). Five minutes later, 500 µL aliquots of the LPS-treated blood are incubated with either 2 µL vehicle (DMSO) or 2 µL of test compound in DMSO for 24 h at 37° C. (for induction of COX-2). Unstimulated control blood at time zero (no LPS) is used as blank. At the end of the 24 h incubation, the blood is centrifuged at 3,000 rpms for 10 min at 4° C. to obtain plasma. The plasma is assayed for $PGE_2$ using an enzyme immunoassay kit (Assay Designs, 901-001) according to the manufacturer's instructions.

2. COX-1 (Clotting-induced $TXB_2$ Production):

Fresh blood from male or female volunteers is collected into vacutainers containing no anticoagulants. These subjects have no apparent inflammatory conditions and have not taken any NSAIDs for at least 7 days prior to blood collection. Aliquots of 500 µL are immediately transferred to polypropylene tubes preloaded with 2 µL of either DMSO or 2 µL of test compound in DMSO. The tubes are vortexed and incubated at 37° C. for 1 h to allow the blood to clot. At the end of the incubation, serum is obtained by centrifugation (3,000 rpms for min at 4° C.). The serum is obtained and is assayed for $TXB_2$ using an enzyme immunoassay kit (Assay Designs, 901-002) according to the manufacturer's instructions.

Representative Rat Paw Edema Assay—Protocol

Male Sprague-Dawley rats (150-200 g) are fasted overnight and are given p.o., either vehicle (1% methocell) or a test compound in the morning. One hr later, a line is drawn using a permanent marker at the level above the ankle in one hind paw to define the area of the paw to be monitored. The paw volume ($V_{Oh}$) is measured using a plethysmometer (Ugo-Basile, Italy) based on the principle of water displacement. The animals are then injected subplantarly with 50 ul of a 1% carrageenan solution in saline (Sigma Chem) into the paw using an insulin syringe with a 25-gauge needle (i.e. 500 ug carrageenan per paw). Three hr later, the paw volume ($V_{3h}$) is measured and the increases in paw volume ($V_{3h}$—$V_{Oh}$) are calculated. Paw edema data are compared with the vehicle-control group and percent inhibition calculated taking the values in the control group as 100%. All treatment groups are coded to eliminate observer bias.

Acute Gastric Erosion Model in Rats

The gastric protective effects of the compounds of the present invention co-administered with aspirin may be evaluated in the following assay.

Male Wistar rats (200-250 g) were fasted for 16-18 h prior to use for experiment. Aspirin, rofecoxib in combination with aspirin (dosed separately), or test compound in combination with aspirin (dosed separately) were given on the morning of the experiment at a dosing volume of 1 ml/kg in 0.5% methocel. Three hr later, the animals were euthanized by $CO_2$ inhalation and the stomach removed, rinsed in saline and prepared for imaging processing. Microscopic pictures of the stomach were taken using a digital camera and gastric erosions were measured using an imaging software by an observer unaware of the treatment groups. The length of gastric erosions was measured in mm and the total length of all erosions from each stomach was obtained and used as gastric damage score.

This model is also described in S. Fiorucci, et al., Gastroenterology, vol. 123, pp. 1598-1606, 2002 and M. Souza, et al., Am. J. Physiol. Gastrointest. Liver Physiol., vol. 285, pp. G54-G61, 2003.

NSAID-induced Gastropathy in Rats

Rationale

The major side effect of conventional NSAIDs is their ability to produce gastric lesions in man. Rats are sensitive to the actions of NSAIDs and have been used commonly in the past to evaluate the gastrointestinal side effects of current conventional NSAIDs. In the present assay, NSAID-induced gastrointestinal damage is observed by measuring urinary $^{51}Cr$ excretion after oral dosing of $^{51}Cr$-EDTA. Urinary $^{51}Cr$ excretion is a well-established and sensitive technique to detect gastrointestinal integrity in animals and man.

Methods

Male Sprague-Dawley rats (150-200 g) are administered orally a test compound either once (acute dosing) or in multiple doses for a few days (chronic dosing). Immediately after the administration of the last dose, the rats are given an oral dose of $^{51}Cr$-EDTA (10 µCi/rat). The animals are placed individually in metabolism cages with food and water ad lib. Urine is collected for a 24 hr period and $^{51}Cr$ urinary excretion is calculated as a percent of total ingested dose.

Protein-Losing Gastropathy in Squirrel Monkeys

Rationale

Protein-losing gastropathy (manifested as appearance of circulating cells and plasma proteins in the GI tract) is a significant and dose-limiting adverse response to NSAIDs. This can be quantitatively assessed by intravenous administration or $^{51}CrCl_3$ solution. This isotopic ion can avidly bind to cell and serum globins and cell endoplasmic reticulum. Measurement of radioactivity appearing in feces collected for 24 hr after administration of the isotope thus provides a sensitive and quantitative index of protein-losing gastropathy.

Methods

Groups of male squirrel monkeys (0.8 to 1.4 kg) are treated by gavage with 1% methocel or a test compounds at multiple doses for a few days. Intravenous $^{51}Cr$ (5 µCi/kg in 1 ml/kg PBS) is administered 1 hr after the last drug/vehicle dose, and feces collected for 24 hr in a metabolism cage and assessed for excreted $^{51}$Cr by gamma-counting. $^{51}$Cr fecal excretion is calculated as a percent of total injected dose.

Rat Aortic Smooth Muscle Rings in Male Sparague-dawley Rats

Preparation of Rat Aortic Smooth Muscle Rings

Male Sprague-Dawley rats (Charles River Laboratories (Wilmington, Mass.) are euthanized by intraperiton injection of a high dose of sodium pentobarbitone (80-100 mg/kg). The thoracic aorta is rapidly excised and immediately placed in a Petri dish containing warn (37° C.) oxygenated (95% 0, and 5% $CO_2$) Kreb's buffer (composition per millimolar: NaCl (119); KCI (4.69); $CaCl_2.H_2O$ (2.52); $MgSO_4.7H_2O$ (0.57); $NaHCO_2$, (25); $NaH_2PO_4.H_2O$ (1.01) and glucose (11.1)}. Under a stereoscopic dissecting microscope, the aorta is cleaned, freed from adhering fat and connective tissues. The tissue is cut into ring segments, each approximately 2-3 mm in length.

For experiments to measure relaxation of the tissue under various conditions, a stainless steel tissue holder and a U-shaped stainless steel wire are inserted into the lumen of the aortic ring. The tissue holder anchored the ring at the bottom of the organ bath whereas the end of the U-shaped steel wire is tied with fine silk thread so that it connected to the FT-202 transducer. The tissue holder and the steel wire along with the aortic ring are then suspended in a 5-ml, double-jacketed temperature-controlled glass organ bath (Radnoti Glass Technology, Inc., Monrovia, Calif.) filled with fresh Kreb's buffer. A mixture of 95% $O_2$ and 5% $CO_2$ is bubbled through a porous sintered disc at the bottom of the bath. The rings are given an initial resting tension of 1.5 g and the preparation is allowed to equilibrate at the initial tension for about 90 minutes. During this equilibration period, the bath fluid is changed every 15 minutes and replaced with fresh prewarmed (37° C.) Kreb's buffer. The isometric tension of the aortic muscle at rest and its response to different stimuli are recorded on a Power Macintosh 6100 computer via a MacLab 8/S computer interface (CB Sciences, Inc, Milford, Mass.) after an initial amplification through a low-noise ETH-400 bioamplifier (CB Sciences, Inc, Milford, Mass.). Contractile responsiveness of the tissue strips is established with 10 TM phenylephrine, and the strips are incubated with the drug for 20 minutes to establish a steady level of contraction.

To test the relaxation effects, test compounds can be added to the phenylephrine precontracted strips in the tissue bath at cumulative concentrations of 0.1 PI to 0.1 mM. Concentration of test compounds may be increased only after relaxation at the previous concentration had reached a plateau level.

Representative Examples

The invention will now be illustrated by the following non-limiting examples in which, unless stated otherwise:

(i) all operations were carried out at room or ambient temperature, that is, at a temperature in the range 18-25° C.; evaporation of solvent was carried out using a rotary evaporator under reduced pressure (600-4000 pascals: 4.5-30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (NMR) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The following abbreviations have the indicated meanings:
Ac=Acetyl
Bn=Benzyl
DBU=1,8-diazabicyclo[5.4.0]undec-7-ene
DIBAL=diisobutylaluminum hydride
DMAP=4-(dimethylamino)pyridine
DMF=N,N-dimethylformamide
$Et_3N$=Triethylamine
HBSS=Hanks' balanced salt solution
LDA=lithium diisopropylamide
m-CPBA=metachloroperbenzoic acid
MMPP=monoperoxyphtalic acid
MPPM=monoperoxyphthalic acid, magnesium salt $6H_2O$
Ms=methanesulfonyl=mesyl=$S(O)_2Me$
MsO=methanesulfonate=mesylate
NSAID=non-steroidal anti-inflammatory drug
OXONE®=2 $KHSO_5.KHSO_4.K_2SO_4$
PBS=phosphate buffered saline
PCC=pyridinium chlorochromate
PDC=pyridinium dichromate
Ph=Phenyl
Phe=Benzenediyl
Pye=Pyridinediyl
r.t.=room temperature
rac.=Racemic
SAM=aminosulfonyl or sulfonamide or $S(O)_2NH_2$
TBAF=tetra-n-butylammonium fluoride
Th=2- or 3-thienyl
TFAA=trifluoroacetic acid anhydride
THF=Tetrahydrofuran
Thi=Thiophenediyl
TLC=thin layer chromatography
TMS-CN=trimethylsilyl cyanide
Tz=1H (or 2H)-tetrazol-5-yl
$C_3H_5$=Allyl Alkyl Group Abbreviations
Me=Methyl
Et=Ethyl
n—Pr normal propyl
i—Pr=Isopropyl
n-Bu=normal butyl
i-Bu=Isobutyl
s-Bu=secondary butyl
t-Bu=tertiary butyl c—Pr=Cyclopropyl
c-Bu=Cyclobutyl
c-Pen=Cyclopentyl
c-Hex=Cyclohexyl Methods of Synthesis

EXAMPLE 1

4-[4-Acetoxy-2-(3,4-difluoro-phenyl)-3-(4-methanesulfonyl-phenyl)-but-2-enoyloxy]-2-(3,4-difluorophenyl)-3-(4-methanesulfonyl-phenyl)-but-2-enoic acid, sodium salt

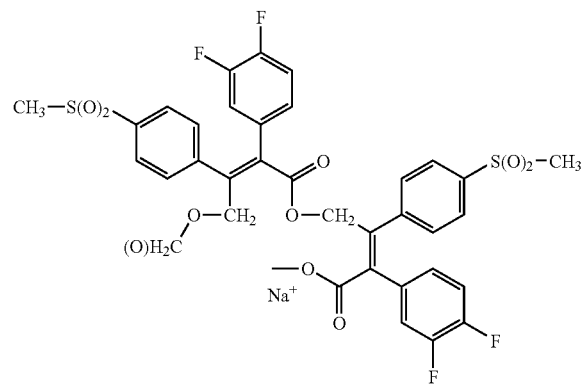

Diisobutylaluminum hydride (1.0 M solution in dichloromethane) was added dropwise to a solution of 3-(3,4-Difluoro-phenyl)-4-(4-methanesulfonyl-phenyl)-H-furan-2-one (15.0 g, 42.8 mmol) and $CH_2Cl_2$ at 0° C. Upon completion of the addition, the solution was allowed to warm to rt, and maintained for 12 h. The reaction mixture was quenched by the addition of a saturated solution of sodium potassium tartrate. Celite was added, and the resulting mixture was filtered. The aqueous layer was extracted with $CH_2Cl_2$. The combined extracts were dried ($MgSO_4$) and concentrate to afford 2-(3,4-Difluoro-phenyl)-3-(4-methanesulfonyl-phenyl)-but-2-ene-1,4-diol as a pale yellow solid: $^1H$ NM ($CDCl_3$, 500 MHz) δ 7.74 (d, 2H), 7.26 (d, 2H), 6.88-6.90 (m, 2H), 7.29-7.31 (m, 1H), 4.52-4.62 (m, 4H), 3.01 (s, 1H). A solution of the crude diol (5.0 g, 14 mmol), $Et_3N$ (2.0 mL, 14 mmol), tert-butyldimethylchlorosilane (2.1 g, 14 mmol), and $CH_2Cl_2$ (100 mL) was maintained at rt for 12 h. The reaction mixture was adsorbed onto silica gel and purified by flash chromatography on silica gel (eluent hexanes/EtOAc) to afford 4-(tert-Butyl-dimethyl-silanyloxy)-3-(3,4-difluoro-phenyl)-2-(4-methanesulfonyl-phenyl)-but-2-en-1-ol as a colorless oil: $^1H$ NMR ($CDCl_3$, 500 mHz), δ 7.38 (dd, 2H), 7.28 (dd, 2H), 6.90-6.92 (m, 1H), 6.65-6.67 (m, 1H), 6.13-6.15 (m, 1H), 4.74 (s, 2H), 4.55 (d, 2H), 2.86 (d, 2H), 0.97 (s, 9H), 0.04 (s, 3H), 0.02 (s, 3H). A solution of acetyl chloride (40 μL, 0.56 mmol) and $CH_2Cl_2$ (10 mL) was added to a cooled (0° C.) solution of 4-(tert-butyl-dimethyl-silanyloxy)-3-(3,4-difluoro-phenyl)-2-(4-methanesulfonyl-phenyl)-but-2-en-1-ol (250 mg, 0.5 mmol), N,N-dimethylaminopyridine (10 mg), $Et_3N$ (150 μL, 0.53 mmol), and $CH_2Cl_2$ (20 mL). After 12 h, the reaction mixture was adsorbed onto silica gel, and purified by flash chromatography on silica gel (eluent EtOAc/hexanes) to afford acetic acid 4-(tert-butyl-dimethyl-silanyloxy)-3-(3,4-difluoro-phenyl)-2-(4-methanesulfonyl-phenyl)-but-2-enyl ester as a colorless oil: $^1H$ NMR ($CDCl_3$, 500 mHz), δ 7.74 (d, 2H), 7.24 (d, 2H), 7.22-7.28 (m, 2H), 6.66-6.69 (m, 1H), 5.08 (s, 2H), 4.60 (s, 2H), 3.00 (s, 3H), 2.05 (s, 3H), 0.92 (s, 9H), 0.00 (s, 3H), −0.02 (s, 3H). Hydrogen fluoride/pyridine complex (500 μL) was added to a solution of acetic acid 4-(tert-butyl-dimethyl-silanyloxy)-3-(3,4-difluoro-phenyl)-2-(4-methanesulfonyl-phenyl)-but-2-enyl ester (130 mg, 0.28 mmol) and $CH_2Cl_2$ (10 mL). After 10 min, the solution was quenched by the addition of saturated aqueous $NaHCO_3$ solution until a pH of 7 was achieved. The mixture was extracted with $CH_2Cl_2$, and the combined extracts were dried ($MgSO_4$). The crude extracts were treated with Dess-Martin periodinane (146 mg, 0.35 mmol). After 1 h, $H_2O$ was added (1 mL) and the resulting slurry was stirred vigorously for 20 min. The mixture was filtered through a plug of silica gel (eluent: EtOAc). The solution was concentrated and dissolved in THF (4 mL), 2-methyl-2-propanol (4 mL), and solution of 2-methyl-2-butene (2.0 M solution in THF, 2 mL). A solution of $NaClO_2$ (131 mg, 1.5 mmol), $NaH_2PO_4$ (241 mg, 2.0 mmol) and $H_2O$ (4 mL) was added. After 10 min, the mixture was diluted with EtOAc (20 mL) and washed with saturated aqueous $NH_4Cl$ solution (5 mL), dried ($MgSO_4$), and filtered to afford 4-Acetoxy-2-(3,4-difluoro-phenyl)-3-(4-methanesulfonyl-phenyl)-but-2-enoic acid: $^1H$ NMR ($CDCl_3$, 500 mHz) δ 7.80 (d, 2H), 7.39 (d, 2H), 7.02-7.05 (m, 2H), 6.85-6.87 (m, 1H), 5.27 (s, 2H), 3.06 (s, 3H), 1.93 (s, 3H). The crude 4-acetoxy-2-(3,4-difluoro-phenyl)-3-(4-methanesulfonyl-phenyl)-but-2-enoic acid (100 mg, 0.24 mmol) was combined with 4-(tert-Butyl-dimethyl-silanyloxy)-3-(3,4-difluoro-phenyl)-2-(4-methanesulfonyl-phenyl)-but-2-en-1-ol (114 mg, 0.24 mmol), triphenylphosphine (70 mg, 0.27 mmol), and THP (100 μL). The mixture was sonicated until a solution was observed. Diispropylazodicarboxylate (53 μL, 0.27 mmol) was added dropwise via syringe. The mixture was sonicated for 1 h or until all starting material was consumed by LC. The mixture was adsorbed onto silica gel, and purified by flash chromatography on silica gel (eluent: EtOAc/hexanes) to afford 4-acetoxy-2-(3,4-difluoro-phenyl)-3-(4-methanesulfonyl-phenyl)-but-2-enoic acid 4-(tert-butyl-dimethyl-silanyloxy)-3-(3,4-difluoro-phenyl)-2-(4-methanesulfonyl-phenyl)-but-2-enyl ester as a colorless solid: $^1H$ NMR ($CDCl_3$, 500 mHz) δ 7.77 (d, 2H), 7.69 (d, 2H), 7.22 (d, 2H), 7.11 (d, 2H), 6.75-6.94 (m, 3H), 6.68-6.73 (m, 2H), 6.49-6.51 (m, 1H), 5.32 (s, 2H), 5.09 (s, 2H), 4.58 (s, 2H), 3.03 (s, 3H), 3.02 (s, 3H), 1.90 (s, 3H), 0.85 (s, 9H), 0.01 (s, 3H), 0.00 (s, 3H). A solution of 4-acetoxy-2-(3, 4-difluoro-phenyl)-3-(4-methanesulfonyl-phenyl)-but-2-enoic acid 4-(tert-butyl-dimethyl-silanyloxy)-3-(3,4-difluoro-phenyl)-2-(4-methanesulfonyl-phenyl)-but-2-enyl ester (72 mg, 0.084 mmol) and $CH_2Cl_2$ (5 mL) was treated with HF/pyridine complex (0.5 mL). After 10 min, the reaction was quenched by the addition of saturated aqueous $NaHCO_3$ (5 mL). The mixture was extracted with $CH_2Cl_2$, and the combined extracts were dried ($MgSO_4$). The crude extracts were treated with Dess-Martin periodinane (46 mg, 0.11 mmol). After 1 h, $H_2O$ was added (1 mL) and the resulting slurry was stirred vigorously for 20 min. The mixture was filtered through a plug of silica gel (eluent: EtOAc). The solution was concentrated and dissolved in THF (4 mL), 2-methyl-2-propanol (4 mL), and a solution of 2-methyl-2-butene (2.0 M solution in THF, 2 mL). A solution of $NaClO_2$ (40 mg, 0.44 mmol), $NaH_2PO_4$ (73 mg, 0.61 mmol) and $H_2O$ (4 mL) was added. After 10 min, the mixture was diluted with EtOAc (20 mL) and washed with saturated aqueous $NH_4Cl$ solution (5 mL), dried ($MgSO_4$), filtered, and purified on flash chromatography on silica gel (eluent: $CH_2Cl_2$/MeOH to afford 4-[4-Acetoxy-2-(3,4-difluoro-phenyl)-3-(4-methanesulfonyl-phenyl)-but-2-enoyloxy]-2-(3,4-difluoro-phenyl)-

3-(4-methanesulfonyl-phenyl)-but-2-enoic acid as a colorless solid. The sodium salt of the acid was prepared by dissolving the acid in the minimum amount of EtOH, cooling the solution to 0° C., and adding 1 equivalent of aqueous NaHCO$_3$. The sodium salt of the title compound was isolated after freeze-drying: $^1$H NMR (D$_2$O, 500 MHz) δ 7.58 (d, 2H), 7.50 (d, 2H), 7.16 (d, 2H), 7.14 (d, 2H), 6.88-6.91 (m, 2H), 6.71-6.86 (m, 2H), 6.54-6.57 (m, 1H), 6.43-6.46 (m, 1H), 5.22 (s, 2H), 4.68 (s, 2H), 3.04 (s, 3H), 3.00 (s, 3H), 1.75 (s, 3H).

Following the procedures provided in Example 1, by substitution of the appropriate X, Y and Z groups or X$^1$, Y$^1$ and Z$^1$ groups, the following non-limiting illustrative compounds may also be prepared.

TABLE 1

(Illustrative compounds of Formula I)

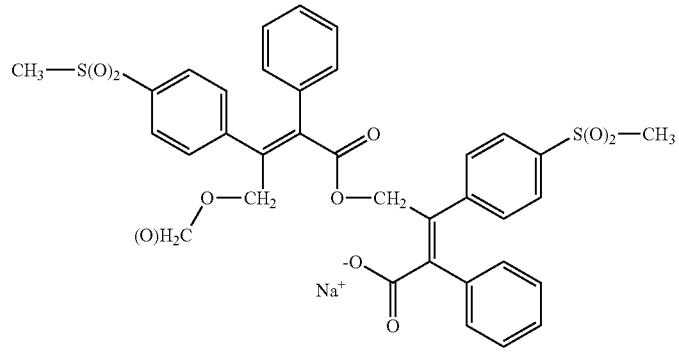

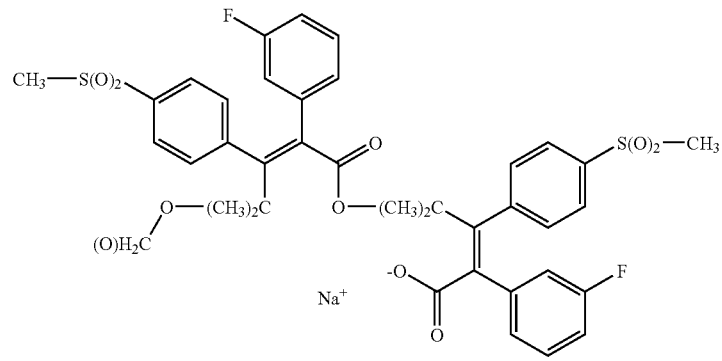

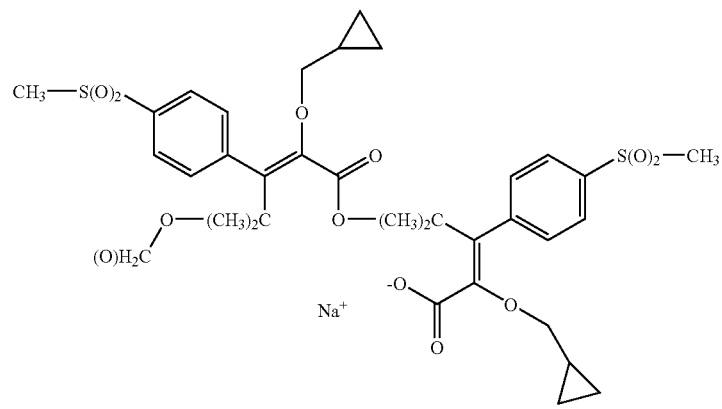

TABLE 1-continued
(Illustrative compounds of Formula I)
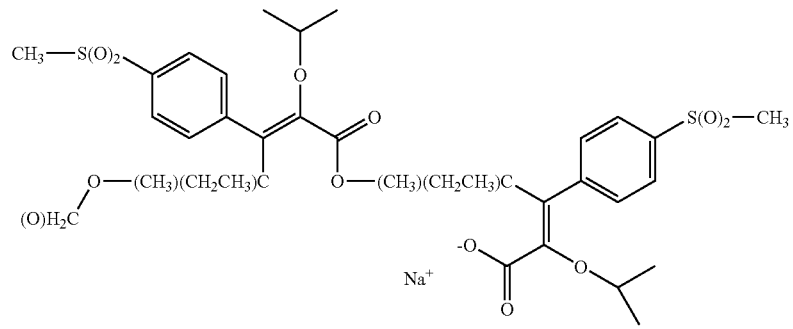
TABLE 2
(Illustrative compounds of Formula II)
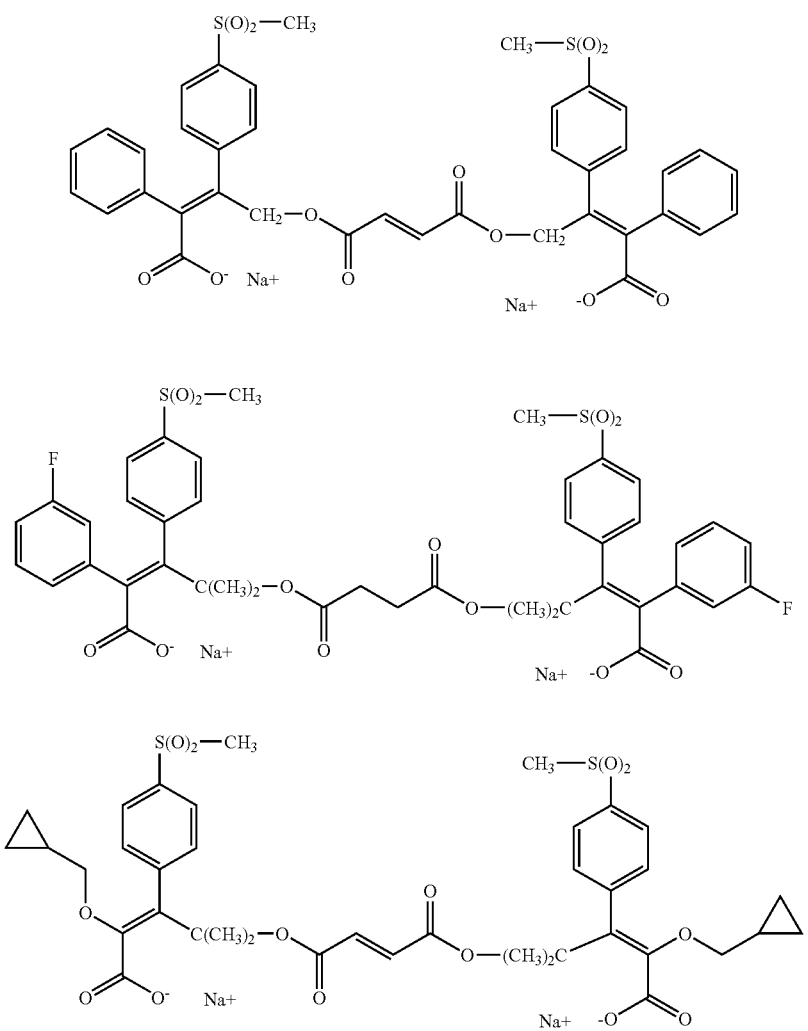

TABLE 2-continued (Illustrative compounds of Formula II)

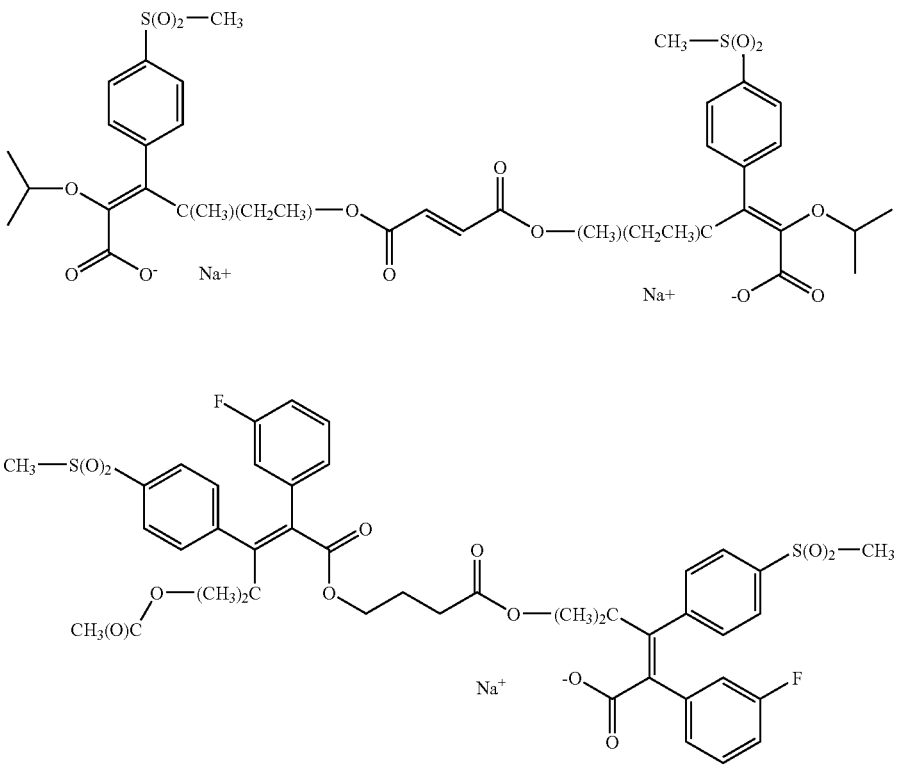

What is claimed is:

1. A compound of Formula I or Formula II

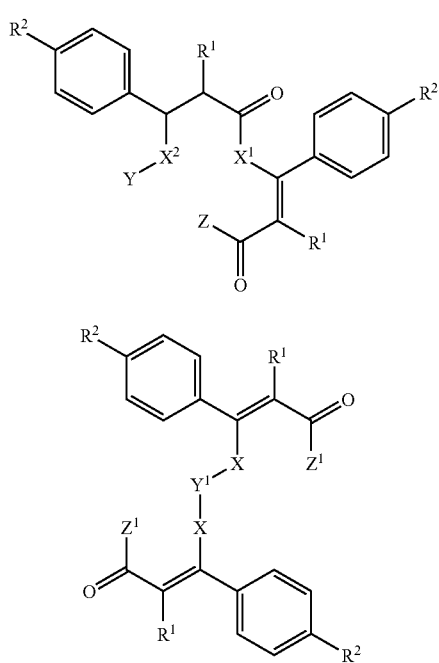

or pharmaceutically acceptable salt thereof, wherein
$R^1$ is selected from the group consisting of
  (a) phenyl, optionally substituted at positions 3 and 4 halogens,
  (b) —O-isopropyl,
  (c) —O-cyclopropyl, and
  (d) —O—CH$_2$-cyclopropyl;
$R^2$ is selected from the group consisting of:
  (a) —S(O)$_2$CH$_3$, and
  (b) —S(O)$_2$NH$_2$;
$R^3$ is selected from the group consisting of
  (a) hydrogen,
  (b) methyl,
  (c) ethyl,
  (d) hydroxyl,
  (e) F, Cl, and
  (f) CF$_3$;
$R^4$ is selected from the group consisting of
  (a) methyl, and
  (b) ethyl;
$X^1$ is selected from the group consisting of:
  (a) —OCH$_2$—,
  (b) —OC(R$^3$)(R$^4$)—,
  (c) —CH$_2$-linker —O—, and
  (d) —C(R$^3$)(R$^4$)-linker-O—,
wherein the oxygen end of $X^1$ is attached to the carbonyl carbon of Formula I;
$X^2$ is selected from the group consisting of:
  (a) —OCH$_2$—,
  (b) —OC(R$^3$)(R$^4$)—, (c) —CH$_2$-linker-O—, and
(d) —C(R$^3$)(R$^4$)-linker-O—;
wherein the carbon end of X$^2$ is attached to the carbon adjacent to the R$^2$-phenyl explicitly shown;
-linker— is selected from the group consisting of
(a) —C(O)—(CH2)$_m$—O—,
(b) —C(O)—(CH$_2$)$_m$(—O—(CH$_2$)n)$_p$—O—, and
(c) —C(O)-aryl-O—,
wherein m, n and p are each independently integers ranging from 0 to 6;
Y is selected from the group consisting of
(a) hydrogen, and
(b) acyl,
wherein the acyl group is selected from the group consisting of
(a) —C(O)—C$_{1-6}$alkyl, optionally substituted with 1, 2 or 3 substituents independently selected from the group consisting of halo, hydroxyl, amino, C$_{1-3}$alkoxy, aminoC$_{1-3}$alkyl,
(b) —C(O)-aryl, and
(c) an amino acid;
Z is selected from the group consisting of:
(a) —OR$^5$,
(b) —NR$^5$R$^6$,
wherein R$^5$ and R$^6$ are each independently selected from
(a) hydrogen,
(b) C$_{1-6}$alkyl,
(c) phenyl, and
(d) C$_{1-2}$-phenyl,
wherein R$^5$ and R$^6$ choices (b), (c) and (d) are optionally substituted with 1, 2, or 3 substituents selected from halo, hydroxyl, amino, C$_{1-3}$alkyl, and C$_{1-3}$alkoxy;
X is selected from the group consisting of:
(a) —OCH$_2$—, and
(b) —C(R$^3$)(R$^4$)O—,
wherein the carbon at the end of X is attached to the carbon adjacent to the phenyl;
Y$^1$ is -linker1-, which is selected from the group consisting of
(a) —C(O)—(CH$_2$)$_r$—C(O)—,
(b) —C(O)-aryl-C(O)—,
(c) —C(O)—(CH$_2$)$_r$—(O—(CH$_2$)$_s$)$_t$—C(O)—, and
(d) —C(O)—(CH$_2$)$_r$—CH—(CH$_2$)$_s$—C(O)—,
wherein r, s and t are each independently integers ranging from 0 to 6; and
Z$^1$ is selected from the group consisting of:
(a) —OR$^5$, and
(b) —NR$^5$R$^6$.

2. A compound according to claim 1 of Formula I

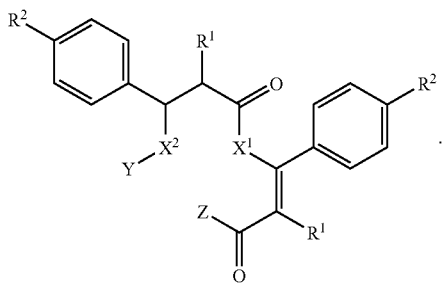

3. A compound according to claim 2 wherein:
R$^1$ is phenyl, optionally substituted at positions 3 and 4 with fluorine.

4. A compound according to claim 2 wherein:
R$^2$ is —S(O)$_2$CH$_3$.

5. A compound according to claim 2 wherein:
R$^3$ is selected from the group consisting of
(a) hydrogen,
(b) methyl, and
(c) ethyl.

6. A compound according to claim 2 wherein:
X$^1$ and X$^2$ are each is selected from the group consisting of:
(a) —OCH$_2$—, and
(b) —OC(R$^3$)(R$^4$)—.

7. A compound according to claim 2 wherein:
Y is hydrogen or —OCH$_3$.

8. A compound according to claim 2 wherein:
Z is hydroxyl or —OCH$_3$.

9. A compound according to claim 2 wherein:
R$^1$ is phenyl, optionally substituted at positions 3 and 4 with fluorine;
R$^2$ is —(O)$_2$CH$_3$;
R$^3$ is selected from the group consisting of
(a) hydrogen,
(b) methyl, and
(c) ethyl;
R$^4$ is selected from the group consisting of
(a) methyl, and
(b) ethyl;
X$^1$ and X$^2$ are each is selected from the group consisting of:
(a) —OCH$_2$—, and
(b) —OC(R$^3$)(R$^4$)—;
Y is hydrogen or —OCH$_3$; and
Z is hydroxyl or —OCH$_3$.

10. A compound according to claim 1 of Formula II

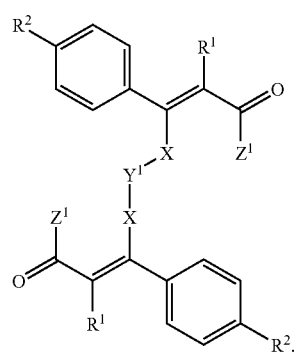

11. A compound according to claim 10 wherein:
R$^1$ is phenyl, optionally substituted at positions 3 and 4 halogens.

12. A compound according to claim 11 wherein:
R$^2$ is —S(O)$_2$CH$_3$.

13. A compound according to claim 12 wherein:
R$^3$ is selected from the group consisting of
(a) hydrogen,
(b) methyl, and
(c) ethyl.

14. A compound according to claim 13 wherein:
Y$^1$ is selected from —(O)C(H)=C(H)C(O)— and —(O)C(CH$_2$)$_2$C(O)—.

15. A compound according to claim 14 wherein:
Z$^1$ is hydroxyl or —OCH$_3$.

16. A compound according to claim 15 wherein:
$R^1$ is phenyl, optionally substituted at positions 3 and 4 halogens;
$R^2$ is —(O)$_2$CH$_3$;
$R^3$ is selected from the group consisting of
  (a) hydrogen,
  (b) methyl, and
  (c) ethyl;

$Y^1$ is selected from —(O)C(H)=C(H)C(O)— and —(O)C(CH$_2$)$_2$C(O)—; and
$Z^1$ is hydroxyl or —OCH$_3$.

17. A pharmaceutical composition comprising a compound according to claim 1 and a pharmaceutically acceptable carrier.

18. A compound according to claim 1 selected from

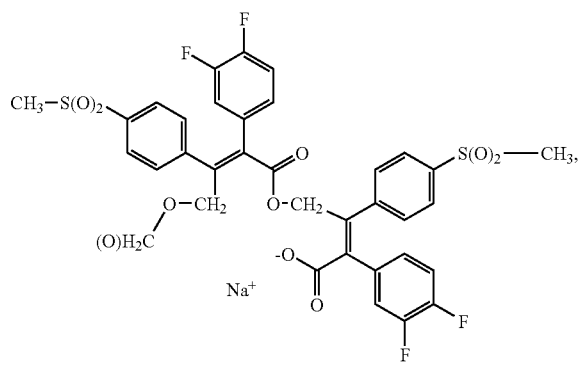

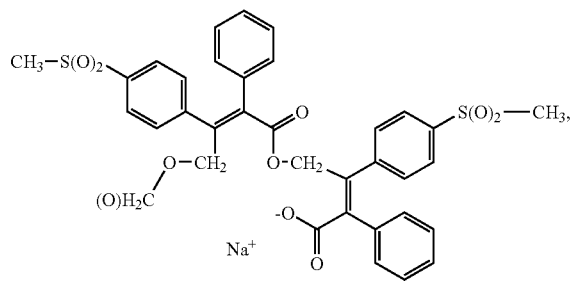

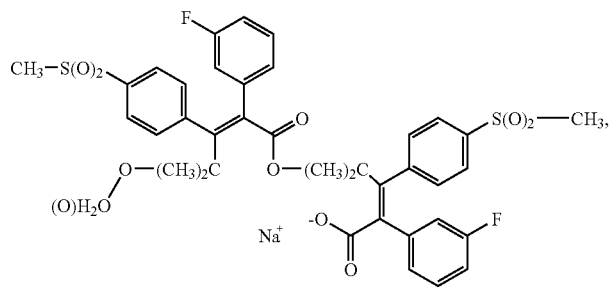

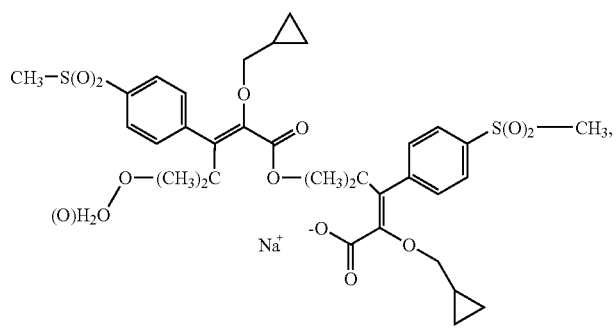

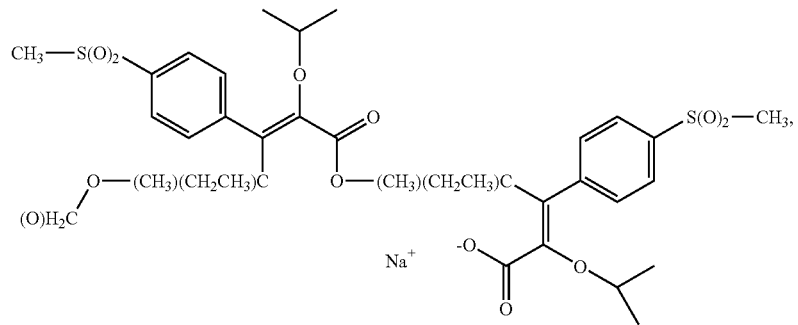
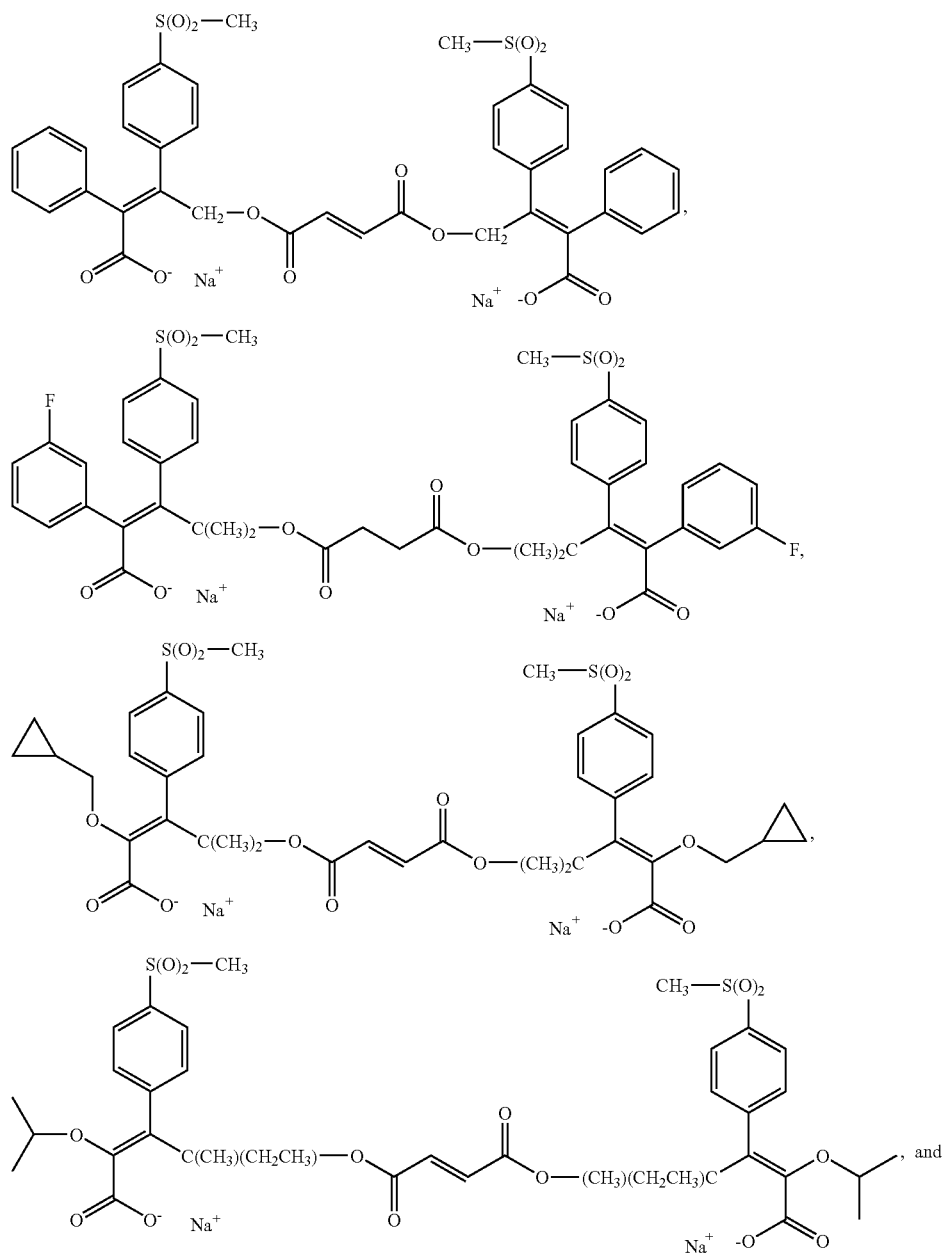

-continued
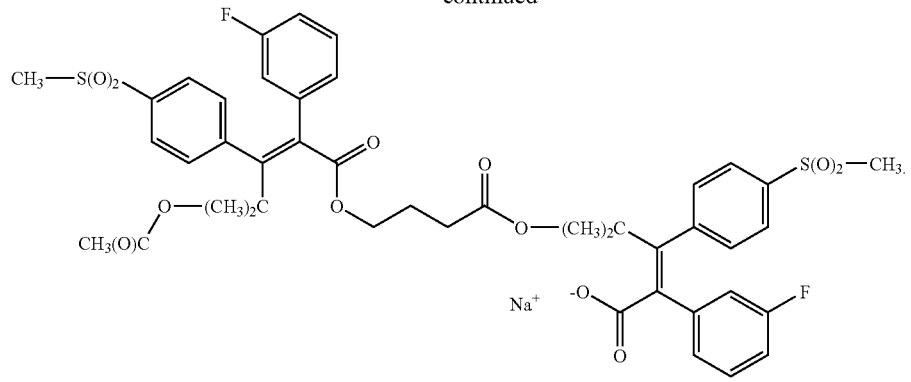
* * * * *